US009123521B2

(12) United States Patent
Verenchikov

(10) Patent No.: US 9,123,521 B2
(45) Date of Patent: Sep. 1, 2015

(54) ELECTRON IMPACT ION SOURCE WITH FAST RESPONSE

(71) Applicant: LECO Corporation, St. Joseph, MI (US)

(72) Inventor: Anatoly N. Verenchikov, St. Petersburg (RU)

(73) Assignee: LECO Corporation, St. Joseph, MI (US)

( * ) Notice: Subject to any disclaimer, the term of this patent is extended or adjusted under 35 U.S.C. 154(b) by 0 days.

(21) Appl. No.: 14/397,274

(22) PCT Filed: Apr. 26, 2013

(86) PCT No.: PCT/US2013/038388
§ 371 (c)(1),
(2) Date: Oct. 27, 2014

(87) PCT Pub. No.: WO2013/163530
PCT Pub. Date: Oct. 31, 2013

(65) Prior Publication Data
US 2015/0144779 A1    May 28, 2015

Related U.S. Application Data

(60) Provisional application No. 61/638,722, filed on Apr. 26, 2012.

(51) Int. Cl.
*H01J 49/00* (2006.01)
*B01D 59/44* (2006.01)
(Continued)

(52) U.S. Cl.
CPC .......... *H01J 49/147* (2013.01); *G01N 30/7206* (2013.01); *H01J 49/40* (2013.01)

(58) Field of Classification Search
USPC .............. 250/306, 307, 309–311, 492.3, 526, 250/281, 282, 287, 288, 299, 427; 361/234, 361/233, 437
See application file for complete search history.

(56) References Cited

U.S. PATENT DOCUMENTS 6,534,764 B1 *   3/2003   Verentchikov et al. ........ 250/287
7,709,789 B2 *   5/2010   Vestal et al. ................... 250/287
(Continued)

FOREIGN PATENT DOCUMENTS

WO    WO-2012/024468 A2    2/2012

OTHER PUBLICATIONS

"A Resonant Electron Capture Time-of-Flight MS with Trochoidal Electron Monochromator", Analytical Chemistry, American Chemical Society, US, vol. 75, No. 13, Jul. 1, 2003, pp. 3001-3009, Voinov V G, et al.
(Continued)

*Primary Examiner* — Bernard E Souw
(74) *Attorney, Agent, or Firm* — Honigman Miller Schwartz and Cohn LLP

(57) ABSTRACT

A closed electron impact ion source with overall opening area of less than 30 mm² is employed for direct and pulsed extraction into a time-flight mass spectrometer in order to enhance sensitivity and immunity to chemical noise of oil and fumes of the vacuum system. For compatibility with dual stage GCxGC separation, the source may contain an inert liner surrounded by an isothermal cage of thermally conductive material. The source inner surface may be reduced to under 100 mm². A portion of carrier gas may be pumped down before admitting the sample and carrier gas into the source. A cooled surface may be used to condense fumes at the analysis time.

21 Claims, 7 Drawing Sheets

(51) Int. Cl.
*H01J 49/14* (2006.01)
*G01N 30/72* (2006.01)
*H01J 49/40* (2006.01)

(56) References Cited

U.S. PATENT DOCUMENTS

2006/0214100 A1* 9/2006 Verentchikov et al. ....... 250/287
2009/0090862 A1   4/2009 Kawana et al.
2010/0301202 A1  12/2010 Vestal
2011/0192969 A1* 8/2011 Verentchikov ................ 250/282
2012/0217391 A1* 8/2012 Shichi et al. .................. 250/306
2013/0020482 A1* 1/2013 Enke et al. .................... 250/282
2013/0048852 A1* 2/2013 Verenchikov ................. 250/282
2013/0206978 A1* 8/2013 Verenchikov et al. ........ 250/282
2013/0313425 A1* 11/2013 Verenchikov ................ 250/282

OTHER PUBLICATIONS

International Search Report dated Mar. 18, 2014, relating to International Application No. PCT/US2013/038388.

* cited by examiner

ELECTRON IMPACT ION SOURCE WITH FAST RESPONSE

This disclosure relates to the area of mass spectroscopic analysis for improving the sensitivity and the response speed of an electron impact ion source for use in, for example, time-of-flight mass spectrometers and fast and two-dimensional gas chromatography.

Electron impact (EI) ionization is employed for environmental analysis and technological control. Samples of interest are extracted from analyzed media, like food, soil or water. The extracts can contain impurities of interest within rich chemical matrixes. Extracts may be separated in time within single or two-dimensional gas chromatography (GC or GCxGC). The GC carrier gas, typically Helium, may deliver the sample into an EI source for ionization by an electron beam. Electron energy may kept at or around 70 eV in order to obtain standard fragment spectra. Spectra may be submitted for comparison against a library of standard EI spectra for identification of compounds. Many applications may demand analysis of ultra-traces at a high level of sensitivity (at least under 1 pg and preferably at 1 fg level) and with a high dynamic range (at least 1E+5 and desirably at 1E+8) between ultra-traces and rich chemical matrix. For improved compound identification it can be preferable to separate compounds using two-dimensional chromatography (GCxGC) to separate individual compounds in time and, accordingly, extract EI spectra of the individual compounds with minimal interference of co-eluting compounds and of chemical noise. It can also be preferable to obtain data with high resolving power for reliable compound identification and for improving ratio of signal to chemical noise.

Since GC and in particular GCxGC separation provide short chromatographic peaks (under 50 ms in GCxGC case) it can be preferable to use a time-of-flight mass spectrometer (TOF MS) for rapid acquisition of panoramic (full mass range) spectra.

One commercial TOF MS with and EI source employs a so-called open EI source with pulsed axial injection into the TOF MS, e.g. Pegasus™ by LECO. The open source accumulates ions within the electron beam and ejects ion packets directly into a reflecting TOF MS. The open source has rapid time response which allows use of the system in a GCxGC analysis. However, the open source can be susceptible to chemical noise, such as residual oil in a related vacuum chamber which can limit the detection limit to 1 pg in GC-MS mode and about 0.1 pg in GCxGC analyses.

Another type employs a continuous so-called "closed" EI source followed by orthogonal acceleration into a reflecting TOF MS, e.g. TruTOF and Pegasus HRT™ by LECO and GCT™ by Waters. The source can provide more immunity to chemical noise, but is known to have slow response, which can limit its application for GCxGC. And, such systems can yield approximately 100 fold ion losses due to spatial losses within the transfer interface between the EI source and the orthogonal acceleration. An attempt of using collisional quadrupoles for reducing ion losses can lead to distortion of the EI spectra and poor matching with library spectra.

As a result, detection limit of commercial GC-TOF and GCxGC-TOF appears limited at approximately 0.1-1 pg level.

Therefore, there is a room for improving sensitivity, immunity to chemical noise, and response time of Electron Impact ion sources for Time-of-flight mass spectrometers.

SUMMARY

The combined EI source parameters can be improved by one or more of the following features:

(i) arranging ion accumulation by an electron beam within a "closed" EI source with subsequent pulsed direct extraction. This can provide nearly 100 fold reduction of a chemical noise level compared to pulsed EI sources employing "open" EI source geometry;

(ii) improving response time of a "closed" EI source by making the source isothermal, preferably using an isothermal shroud comprised of heat conductive materials while using a liner of material having low surface absorption properties; this differs from previous ion sources where low absorbing materials of such sources have low thermal conductivity and, as a result, commonly have cold spots which can cause prolonged sample absorption;

(iii) improving response time of a "closed" EI source by reducing a size of the ionization chamber in order to reduce the absorbing surface, preferably under 100 mm$^2$; this differs from known closed sources having inner surfaces ranging from 500 mm$^2$ to 1000 mm$^2$;

(iv) improving ion source dynamic range and quality of spectra by arranging a 5-10 fold molecular separator within the vacuum chamber and immediately at the entrance of the closed EI ion source, preferably heated to source temperature and pumped by differential port of turbo pump. This differs from prior art molecular separators being used as separate devices remotely located within the atmosphere; and (v) arranging electrostatic positive plugs along the electron beam to thereby focus ions in the ion storage region while generally removing slow secondary electrons; and (vi) tilting the source and steering ion packets for half an angle of ion trajectory tilt and this way improving resolution of the instrument.

As described below, the foregoing features can assist each other in balancing multiple limitations and thus improving the parameters of GCxGC-TOF for ultrasensitive and reliable analysis.

Various implementations will now be described, by way of example only, and with reference to the accompanying drawings in which.

Figure 5:
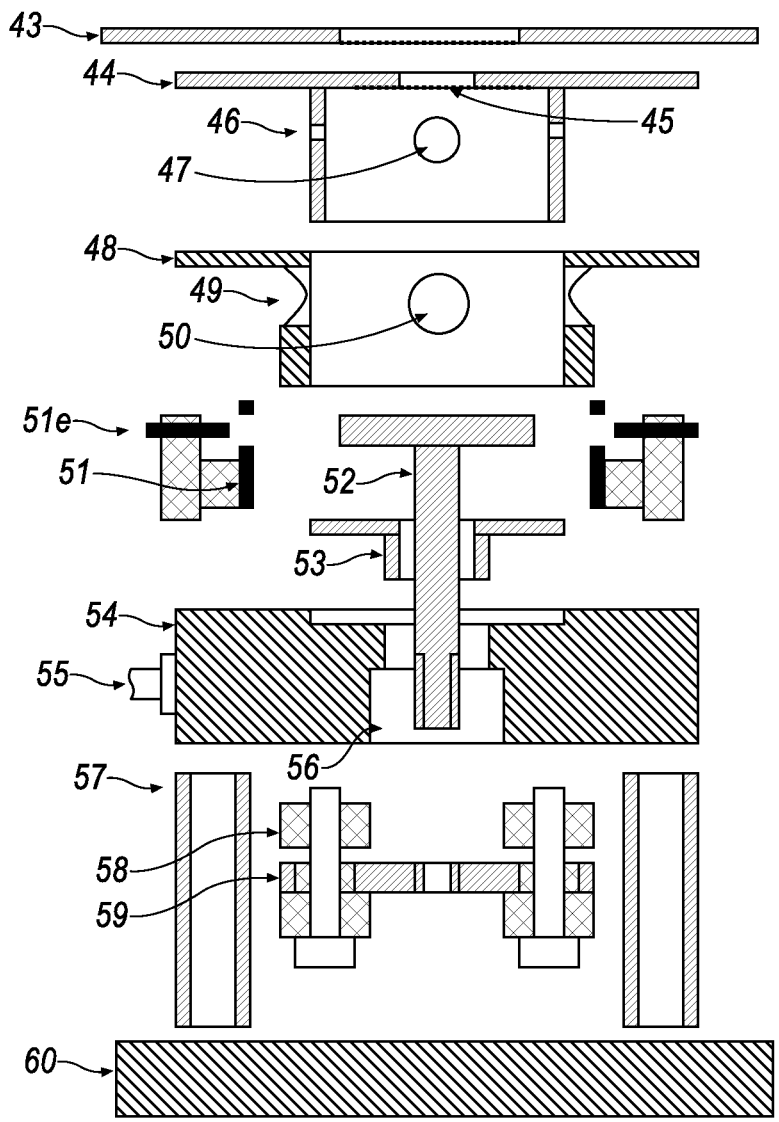
Figure 6:
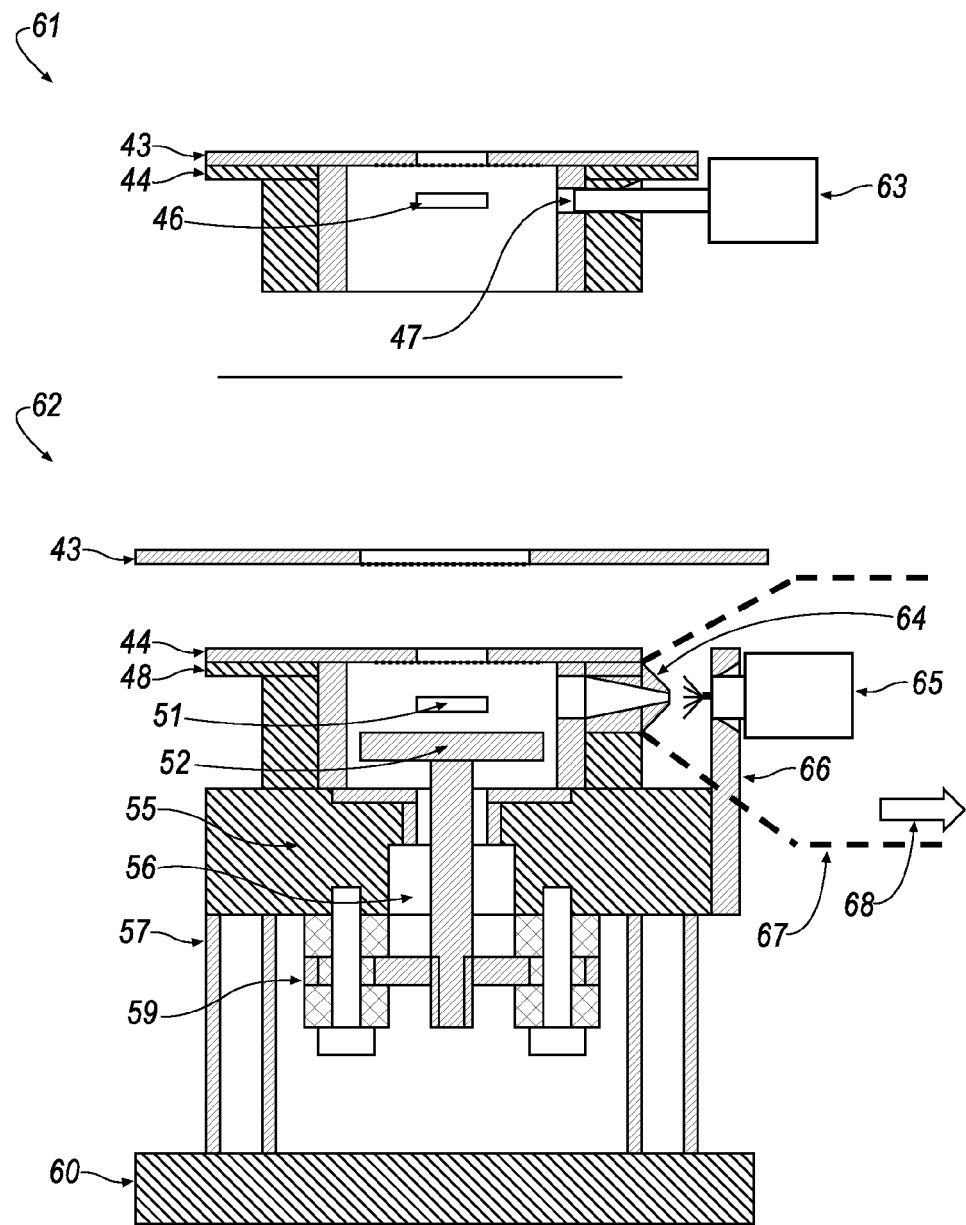
Figure 7:
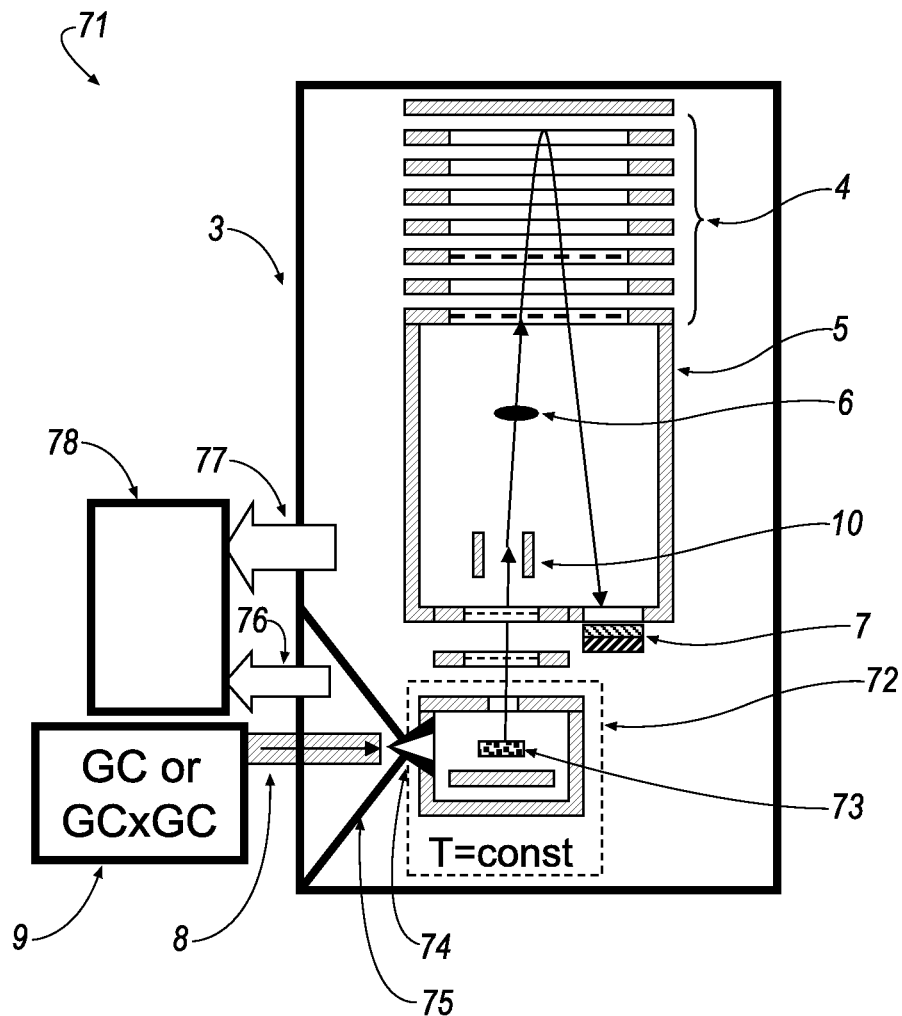

FIG. 5 shown an implementation of an isothermal closed and pulsed ion source in a disassembled format;

FIG. 6 shows an implementation of an isothermal case for a "closed" EI source and an implementation of molecular separator; and FIG. 7 shows an implementation of differential pumping for molecular separator in-front of a "closed" EI source.

DETAILED DESCRIPTION

Figure 1:
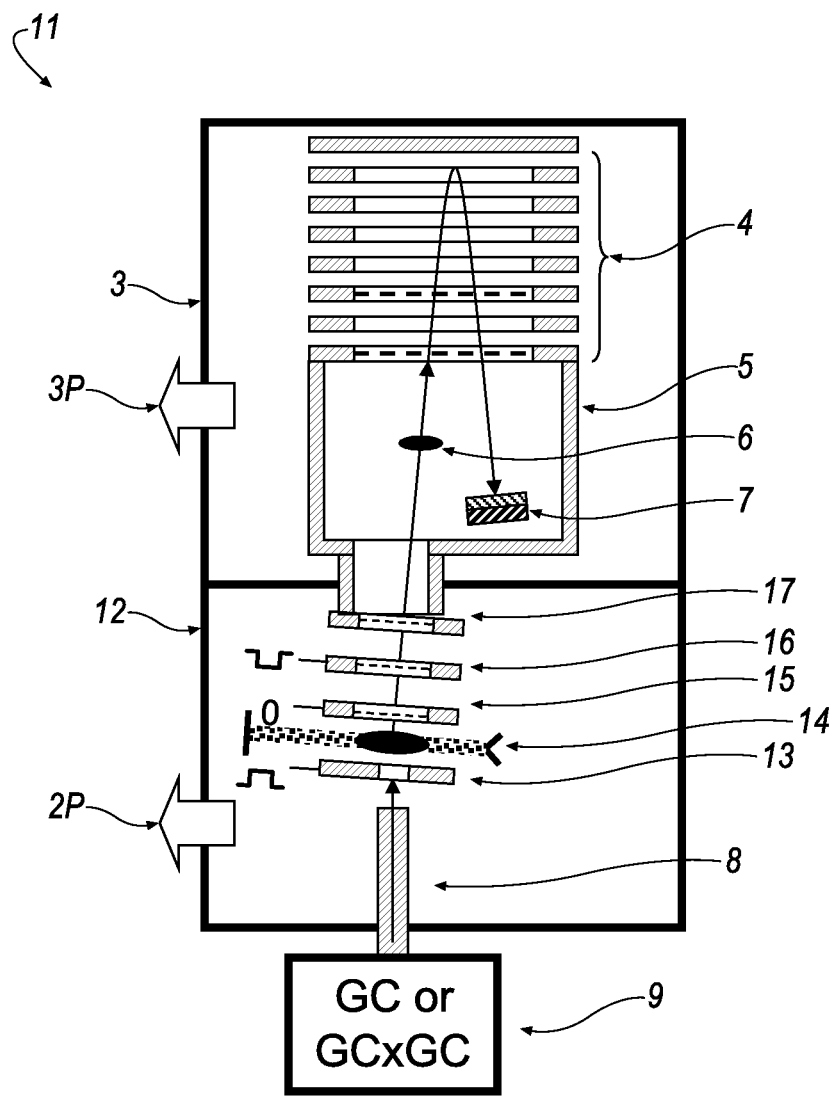
FIG. 1 depicts an "open" EI source with axial pulsed injection into a TOF MS.

Referring to FIG. 1, a TOF MS with a pulsed EI ion source 11 is shown and employs an axial injection scheme and comprises an "open" and pulsed ion source 12 that is coaxially aligned with a reflecting TOF MS 3. The ion source 12 comprises parallel electrodes covered by meshes—push plate 13, ground mesh 15, pull mesh 16, acceleration mesh 17, and an electron emitter 14. As depicted, source 12 is pumped by turbo pump 2P. In an implementation, the reflecting TOF spectrometer 3 comprises an ion mirror 4 (either single or dual stage), electrode covering field-free space 5, and a detector 7. Source 12 and detector are tilted at a small angle to clear a tilted ion path and to compensate aberrations caused by ion packet width.

In operation, vapors of analyzed sample (analyte) may be separated in time within a single or dual stage gas chromatograph 9 and via a heated transfer line 8 as they enter an ionization space that is defined between electrodes 13 and 15. In an implementation, turbo-pump 2P can sustain gas pressure at mid 1E-5 Torr at a standard helium flow of 1 mL/min. A continuous electron beam from the electron emitter 14 (e.g., operating at 70 ev) bombards the sample, thereby producing ions of analyte within the ionization space. Electron beam may generate a potential well to attract ions and correspondingly trap them. Periodically electrical pulses may then be applied to plates 13 and 16 which, in turn, may block penetration of the electron beam and accelerate ions ejected as ion packets 6 into the TOF MS 3. Accordingly, ions are reflected within mirror 4 and onto detector 7.

The foregoing system may be recognized as the standard technique for GCxGC analysis, since the "open" source does not distort fast (20-50 ms wide) GC profiles. Compared to alternative "closed" EI sources, the open EI source may be used for its robustness (as it has lower surface contamination due to a much lower analyte concentration), and comparable sensitivity (lower ionization efficiency is compensated by ion storage within the source.) On the other hand, the "open" source can be disadvantaged when a signal includes a higher chemical background, such as oil from a vacuum pump and the like.

The detection limit (LOD) of the open source appears to not be limited by intensity of an ion signal, but due to the chemical background of standard vacuum systems having typical flux of 10-100 pg/sec per any medium mass component. To achieve femtogram LOD one may desire to employ either oil-free vacuum pumping system or to employ "closed" source geometry.

Figure 2:
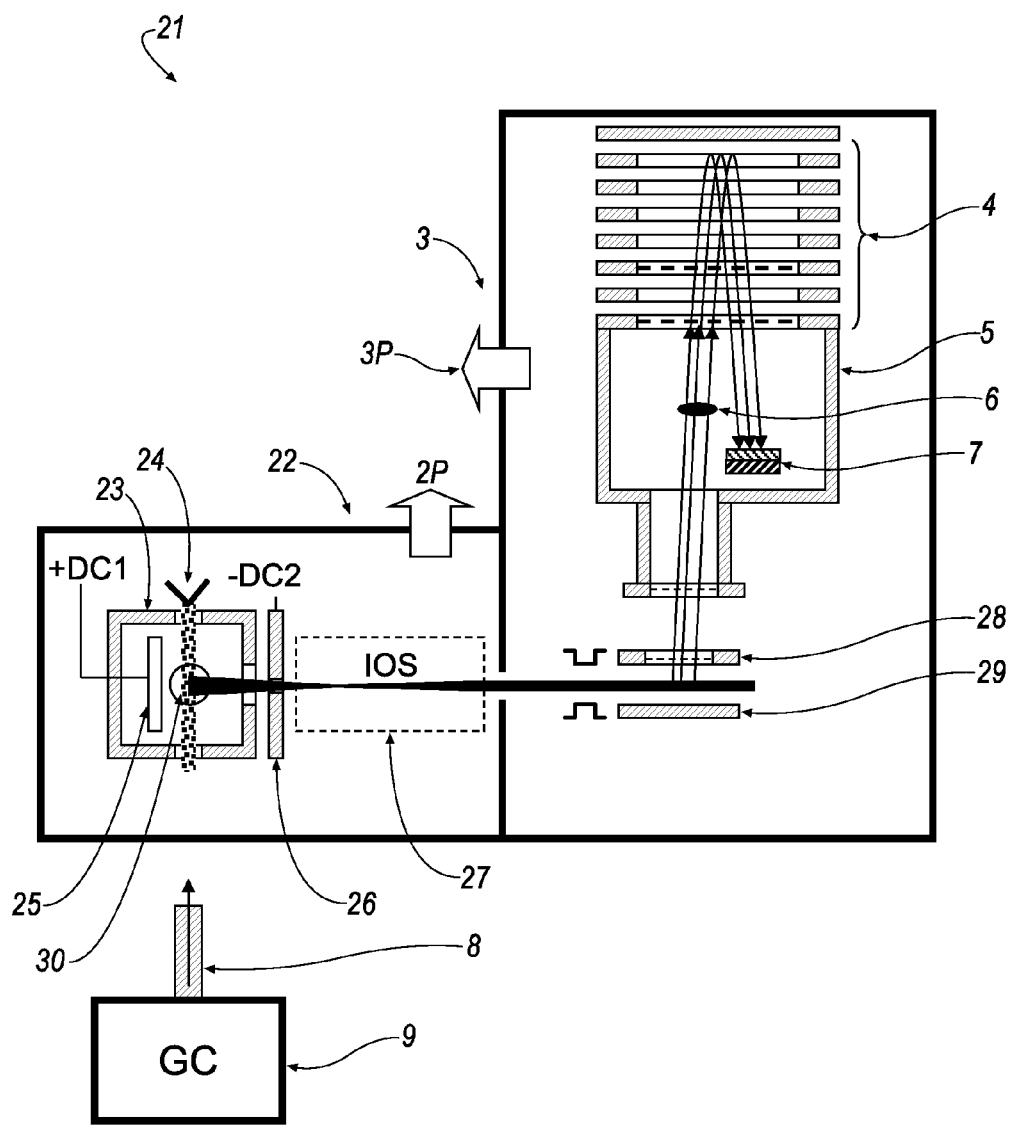
FIG. 2 depicts a closed EI source with an orthogonally accelerating TOF MS.

Referring to FIG. 2, an EI-TOF MS 21 with a "closed" ion source is depicted and provides a continuous electron impact ion source 22 in combination with a reflecting TOF MS 3, wherein the TOF MS 3 is equipped with an orthogonal accelerator using pulsed electrodes 28 and 29. As depicted, the closed source 22 comprises an enclosed ionization chamber 23, an electron emitter 24, a repeller 25, and an extractor 26. The ionization chamber 23 has a port 30 for sealed fit of a transfer line 8 from GC 9. In an implementation, the source may be followed by a transfer ion optical system 27, usually composed of electrostatic lenses and steering plates (not shown). The ion source region 22 and TOF MS analyzer 3 may be pumped by turbo pumps 2P and 3P.

In operation, vapors of analyzed sample (analyte) are introduced into ionization chamber 23. Continuous electron beam generated by emitter 24 (e.g., operating at 70 ev) bombards the sample, thereby producing ions of analyte. A weak electrostatic field of repeller 25 and extractor 26 may be used to continuously extract ions out of the chamber 23. Ion optics 27 are used to deliver the continuous ion beam into the region between plates 28 and 29. Periodically, electrical pulses may then be applied to plates 28 and 29 which, in turn, may block penetration of the continuous ion beam and accelerate ions which already filled the accelerator space. Ion packets 6 are extracted in an orthogonal direction relative to the direction of continuous ion beam. Ion packets, accordingly, become reflected by ion mirror 4 and onto detector 7.

Continuous ion source and orthogonal accelerating TOF MS can be used to provide higher mass resolution of a TOF MS analyzer as the divergence of continuous ion beam can be trimmed using ion optics 27. An advantage of much higher ionization efficiency of the closed source may be partially lost due to spatial ion losses within the transfer ion optics 27 (experimentally estimated as factor 10) and due to limited duty cycle (typically in the order of 10% at medium m/z range.) Overall, the intensity of ion packets is comparable for both instruments 11 and 21.

The closed source may be poorly suited for GCxGC analysis, since it may yield a slow response time due to the slow pumping of the closed ion source. The spread of GC profiles may be due to (a) reasonably large volume of "closed" sources and (b) non uniform heating of "closed" sources which can yield cold spots thereby inducing prolonged analyte absorption on the source walls. "Closed" source geometry may be better suited for ultra-trace analysis as the source concentrates analyte within the source which can thereby enhance the ratio of an analyte signal relative to a chemical background signal of the source chamber, rubber seals and pumping system by factor of 100 to 1000. Thus, "closed" source may be better suited for ultra-trace GCxGC-TOF analysis if it is desired to fix the reaction time of the closed ion source and remove ion losses beyond the "closed" ion source.

Figure 3:
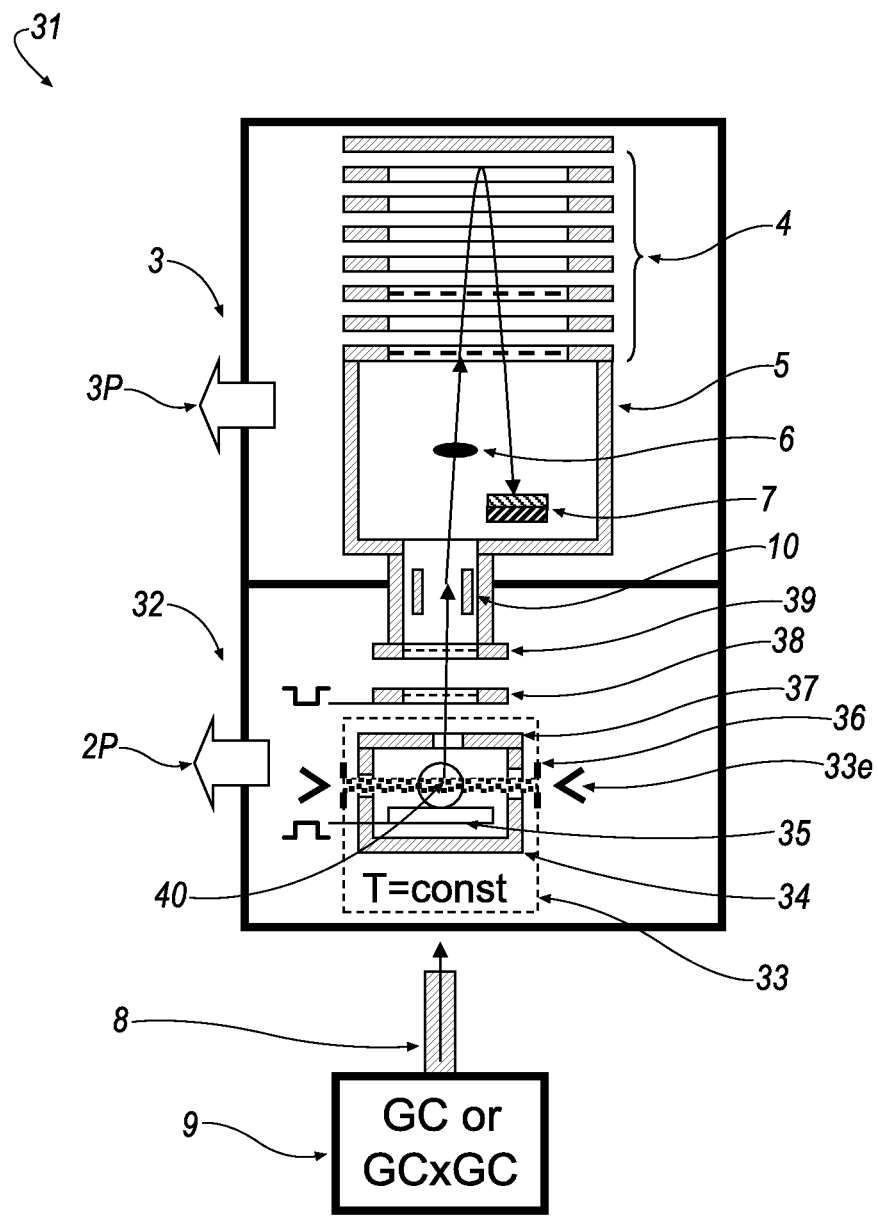
FIG. 3 shows an implementation of a pulsed "closed" EI source.

With reference now to FIG. 3, an implementation of a pulsed "closed" ion source 32 for pulsed axial injection into a reflecting TOF MS 3 is shown. As depicted, pulsed "closed" source 32 may comprise an isothermal envelope 33, an ionization chamber 34 (or source), a pulsed repeller 35, an electron emitter 33e with positively biased slit 36, an exit aperture 37, a pulsed accelerating electrode 38 and a continuous accelerating electrode 39 at accelerating potential of the TOF MS 3. In an embodiment, source chamber 34 may have a sealed inlet 40 for transferline 8 from GCxGC unit 9 and the reflecting TOF MS 3 comprises an ion mirror 4, a shielded drift space 5 and a detector 7. In an implementation, the ion mirror 5 and the detector 7 may be aligned in parallel, and the ion source chamber 34 with accelerating electrodes 35, 37, 38 and 39 may be tilted at half angle of ion trajectory 6. In an implementation, the trajectory tilt of ion packets 6 may be steered by deflectors 10 for another half-angle after ions get fully accelerated. TOF MS and ion source regions may be pumped by turbo-pumps 2P and 3P. In an implementation, the field-free region 5 of the TOF MS may be floated, while the ionization chamber 34 is grounded. In an embodiment, accelerating electrodes 37, 38 and 39 may be covered by fine mesh. In an embodiment, mesh-free accelerating ion optics are used. As depicted, an isothermal cage 33 may be implemented to provide uniform temperature at or between 250 C-300 C on one or more of the walls (e.g., all the walls) of ionization chamber 34 and aperture 37 to restrict cold spots and reduce absorption time when compared to multiple commercial implementations of closed sources. To arrange low absorption time, in an implementation, the source may include a cage of heat conductive material (e.g. aluminum) and an inner liner of low absorbing material (like stainless steel or nickel).

In operation, GCxGC can separate analyte within 1 mL/min carrier gas (typically Helium. Analyte is supplied into the ionization chamber 34 in a carrier flow through a transferline 8, via sealed port 40. As depicted, continuous electron beam from emitter 33e thereafter ionizes the analyte molecules and stores thus formed ions within the electrostatic well of electron beam. In an implementation, a positively biased slit 36 transfers the electron beam, repels ions along the beam, and assists removal of slow secondary electrons formed both in the source and on the opposite emitter. Periodically applied pulses to repeller 35 and extractor 38 extract ion packets into the TOF MS 3 for mass analysis. Ion packets are transferred into the TOF MS which typically have wide spatial and angular acceptance, thus delivering ion packets to the detector without ion losses. Preferably, deflector 7 may be used for both—ion steering towards the detector and for pulsed deflection of Helium ions. Preferably, push pulse on electrode 35 stays on during ion flight to the deflector 7 to avoid any leak of helium ions from the source during the open state of the deflector 7.

Processes within a pulsed closed source using a numerical example will now be provided. It is to be appreciated that while specific values are used and discussed herein, the claims should not be limited to such values unless they are specifically recited therein. For example, and among other possibilities, the exit aperture in the following example is identified as having a 3 mm diameter. However, in an implementation, exit aperture may be between 3 and 10 mm, and in another implementation between 7 and 10 mm. In an embodiment where (i) the enclosed ionization chamber 34 has a diameter and length of 10 mm, i.e. total volume of $V=1$ cm$^3$ and total wall area $S=5$ cm$^2$; and (ii) the exit aperture has 3 mm diameter and the opening area $A=0.1$ cm$^2$. At 1 mL/min Helium flow, the effective pumping speed through 0.1 cm$^2$ at 300 C is 5 L/s, and an estimated gas pressure is 2 mTorr corresponding to mean free path 4 cm (i.e. there is effectively free-molecular regime.) The analyte pumping speed is about 0.5-1 L/s (accounting much larger molecular weight compared to Helium), which is much smaller compared to pumping speed of turbo-pump (i.e. there is substantial concentration of the analyte.) At the same time, the chemical background of the pumping system, from vacuum chamber walls, leaks, and from sealing O-rings is equalized between the vacuum chamber and the ionization chamber. Thus, the ratio of analyte to the source chemical background is substantially improved in closed sources. The inventor speculates that the analyte concentrating factor is between 100 and 1000 compared to open sources, which, in an implementation, at least causes proportional enhancements relative ionization efficiency compared to the chemical background of the pumping system and is likely to enhance ionization efficiency of analyte Vs open sources even accounting larger space charge effects of the concentrated helium ions. Preferably, the ion accumulation time between pulses varies between 50 and 100 μs, while gate opens for 5-10 μs.

Typical time width of chromatographic peaks past GCxGC are about 30-50 ms, thus the goal is to arrive to source parameters which would provide response time in the order of 10 ms. Let us analyze processes of analyte concentration and evacuation within "closed" sources using the same numerical example. Accounting free molecular regime, the evacuation speed of analyte $s=A*\upsilon/4$, where $\upsilon$ is analyte thermal velocity equal to 100 m/s at 300 degC., i.e. $S=1000$ cm$^3$/s. Then evacuation time constant $\tau=V/s=1$ ms. Accounting exponential emptying of the source, the concentration of analyte momentarily spike would be reduced by 4 orders of magnitude in $t=\ln(1E+4)*\tau \sim 10$ $\tau=10$ ms. Thus, the prolonged response time of "closed" sources in order of 1 second for low volatile compounds is not caused by gas dynamic evacuation, but rather by sorption processes on the source walls. Again accounting for the free-molecular regime, and accounting the angular isotropic evaporation, the average number of analyte molecule collisions with source walls can be estimated as $N=A/S \sim 50$ in the considered example. Let us use simple estimate of evaporation time as $\tau_A = 1/f*\exp(W/kT)$, where vibration time $1/f \sim 1E-13$ sec. Results are presented in the below table.

| | Average Absorption time, sec | | | | | El Source Response time, sec | | | |
|---|---|---|---|---|---|---|---|---|---|
| T, C | W = 0.6 eV | W = 0.8 eV | W = 1 eV | W = 1.2 eV | T, C | W = 0.6 eV | W = 0.8 eV | W = 1 eV | W = 1.2 eV |
| 23 | 1.E-03 | 3.E+00 | 8.E+03 | 2.E+07 | 23 | 7.E-02 | 2.E+02 | 4.E+05 | 1.E+09 |
| 50 | 2.E-04 | 3.E-01 | 3.E+02 | 4.E+05 | 50 | 1.E-02 | 1.E+01 | 2.E+04 | 2.E+07 |
| 100 | 1.E-05 | 6.E-03 | 3.E+00 | 1.E+03 | 100 | 6.E-04 | 3.E-01 | 1.E+02 | 7.E+04 |
| 150 | 1.E-06 | 3.E-04 | 7.E-02 | 2.E+01 | 150 | 6.E-05 | 2.E-02 | 4.E+00 | 8.E+02 |
| 200 | 2.E-07 | 3.E-05 | 4.E-03 | 5.E-01 | 200 | 1.E-05 | 1.E-03 | 2.E-01 | 3.E+01 |
| 210 | 2.E-07 | 2.E-05 | 2.E-03 | 3.E-01 | 210 | 6.E-06 | 1.E-03 | 1.E-01 | 1.E+01 |
| 220 | 1.E-07 | 1.E-05 | 1.E-03 | 2.E-01 | 220 | 6.E-06 | 7.E-04 | 7.E-02 | 8.E+00 |
| 230 | 9.E-08 | 9.E-06 | 9.E-04 | 9.E-02 | 230 | 5.E-06 | 5.E-04 | 5.E-02 | 5.E+00 |
| 240 | 7.E-08 | 7.E-06 | 6.E-04 | 5.E-02 | 240 | 4.E-06 | 3.E-04 | 3.E-02 | 3.E+00 |
| 250 | 6.E-08 | 5.E-06 | 4.E-04 | 3.E-02 | 250 | 3.E-06 | 2.E-04 | 2.E-02 | 2.E+00 |
| 260 | 4.E-08 | 3.E-06 | 3.E-04 | 2.E-02 | 200 | 2.E-06 | 2.E-04 | 1.E-02 | 1.E+00 |
| 270 | 3.E-08 | 2.E-06 | 2.E-04 | 1.E-02 | 270 | 2.E-06 | 1.E-04 | 8.E-03 | 6.E-04 |
| 280 | 3.E-08 | 2.E-06 | 1.E-04 | 7.E-03 | 280 | 1.E-05 | 9.E-05 | 6.E-03 | 4.E-01 |
| 290 | 2.E-08 | 1.E-06 | 8.E-05 | 5.E-03 | 290 | 1.E-05 | 7.E-05 | 4.E-03 | 2.E-01 |
| 300 | 2.E-08 | 1.E-06 | 6.E-05 | 3.E-03 | 300 | 9.E-07 | 5.E-05 | 3.E-03 | 2.E-01 |

For "sticky" compounds with W=1 eV, the source response time can be held at 20 ms if generally uniformly heating the ionization chamber to 250° C. However, if there would be cold spots at or around 50° C. lower, the response time rises to 2 seconds. Thus, keeping low response time may be controlled as following: (a) using uniform heating of the EI source, (b) using inner surface materials having lower absorption energies, and (c) minimizing the area of the inner surface of the source.

With respect to the inner surface of the source, while the analyte concentration within the source may be controlled, at least in part, by the area of exit aperture A (concentration is proportional to analyte mass flux divided by pumping speed), the number N of analyte collisions with walls and the source response time $N*\tau_A$ are generally proportional to the ratio of inner surface to aperture surface $N \sim S/A$. Accordingly, a reduction of the source size at a constant aperture size reduces the response time without materially degrading the analyte concentration. In an embodiment, the source size is to be reduced to about 5 mm.

Figure 4:
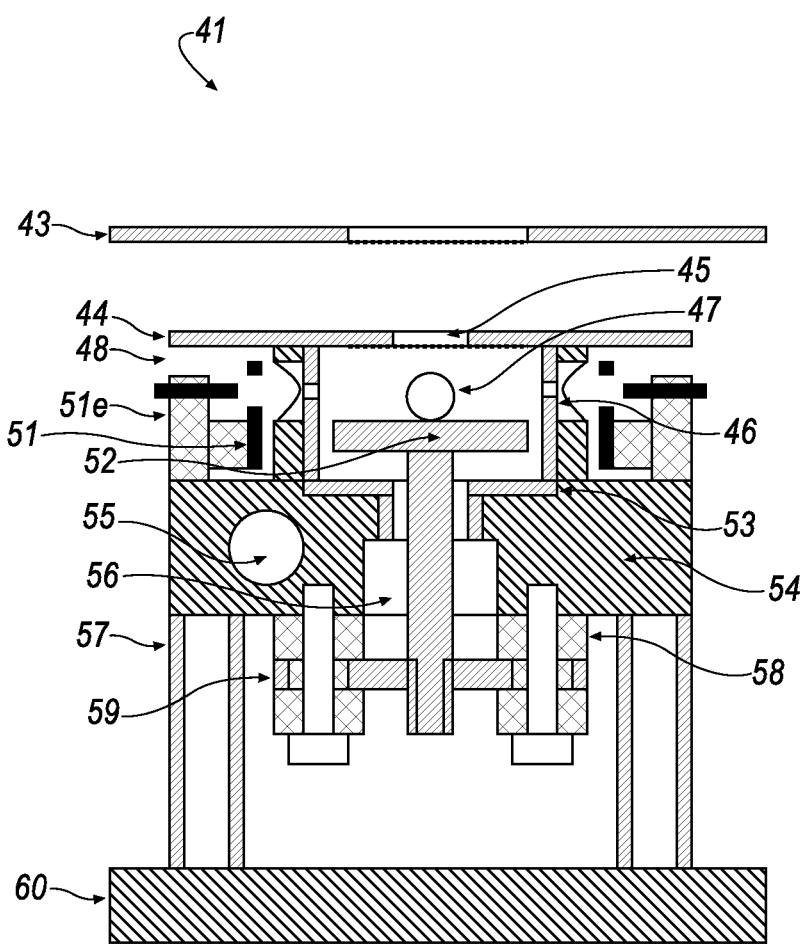
FIG. 4 shows an implementation of an isothermal closed and pulsed ion source in an assembled format.

With reference now to FIG. 4 and FIG. 5, an implementation of an isothermal closed and pulsed ion source 41 is shown in an assembled format and a disassembled format, respectively. In an implementation, source 41 comprises: a pulsed extractor 43, an isothermal cage 48, an electron emitter 51e, a pair of positively biased slits 51, a repeller 52, a bottom liner 53, a base 54 (53 and 54), one or more standoffs 57, ceramic spacers 58 a holder 59 and a vacuum mounting flange 60.

In an implementation, and as shown, pulsed extractor 43 may be covered by mesh.

In an implementation, inner liner 44 is comprised of low absorbing material (e.g. stainless steel) and defines an electron slit 46, a transferline entrance 47 and aperture 45. In an implementation, inner liner 44 may be cover by mesh.

With continued reference to FIG. 4 and FIG. 5, isothermal cage 48 may include thermally conductive material such as, for example aluminum, copper, nickel, or silver. Other materials may be used and the implementation should not be so limited thereby. Further, isothermal cage 48 may include a transfer port 50 and apertures 49 to expose inner liner 44 with electron emitter 51.

As depicted, two electron emitters 51*e* may be provided on opposing sides of source 41. It is to be appreciated, however, that a single electron emitter may be used and the disclosure should not be limited to that which is depicted in the drawings.

In an implementation, base 54 comprises thermally conductive material and includes a heater 55 and a thermocouple (not shown), and defines a venting aperture 56 therein to improve analyte evacuation under the repeller 52.

In an implementation, standoffs 57 are provided between base 54 and vacuum mounting flange 60 and define a volume for isolating ceramic spacers 58, at least a portion of repeller 52 and holder 59. In an implementation, standoffs 57 are fixed, tubular and include material having a generally low thermal conductivity (e.g. stainless tubes).

In an implementation, a source vacuum chamber is provided (not shown) and is made of low absorbing and non-porous materials, like stainless steel. In an implementation, the vacuum chamber may be heated to about 100° C. to prevent accumulation of analyte molecules on the vacuum chamber walls. In an implementation, the source is pumped by a turbo-pump, which may include a filter (e.g., an oil filter). In an implementation, a cold surface (not shown, e.g. Peltier chiller) is introduced within a vacuum chamber to absorb oil and fumes during the operation and to release same in-between analyses.

In operation, the isothermal cage 48 efficiently and rapidly transfers heat from the conductive base 54 and the emitter 51 (e.g., irradiative heat) and equalizes temperature of the ionization chamber that is formed by inner liner 44, bottom liner 53 and repeller 52 thereby preventing irradiative heat losses from inner liners and repeller. Cooling from the top surface of the inner liner 44 can be compensated by effective heat transfer between the wide upper ring of the cage 48 and upper ring of the liner 44. Experimental studies by authors have shown that such ion source can be uniformly heated with less than 10 degree gradients. Substantially simultaneously, the heat conductive material of the base 54 and cage 48 is not exposed to analyte, since the inner surface of the source is formed by relatively inert liners 44 and 53 and by repeller 52. The exemplar source demonstrates that both requirements could be reached: (a) uniform temperature of the source, and (b) low absorbing of materials within ionization chamber.

In an implementation, response time of the closed source may be enhanced through miniaturization. In an embodiment, reducing source size to about 5 mm appears to lead to several advantages. Among others, (a) overall surface area is reduced as a square of the chamber size; (b) irradiative heat loss drops down proportional to the external surface; (c) heat conductivity of walls improves. In an embodiment, the foregoing may allow a source without thermal cage. In such an implementation, the entire chamber may comprise low absorbing material such as, for example, stainless steel or the like.

In an implementation, ion storage may be enhanced by electrostatic repulsion of ions on sides and along the direction of electron beam. In one particular implementation, such repulsion is arranged by forming an electrostatic bias between ion chamber 46 and liner 44 (e.g., isolated by a ceramic spacer) and a push low bias of the repeller 52. In another particular implementation, an additional set of positively biased slits (not shown) are inserted between emitters 51 and the liner 44. As been found in inventor's experiments, the electrostatic side repulsion simultaneously provides an advantage of removing slow electrons from the electron beam region, thus enhancing ion storage capacity and providing "colder", i.e. less excited ion packets.

Few other parameters of the directly extracting pulsed ion source could be estimated based on author's experimental studies which are described in co-pending patent application entitled "Time-of-flight Mass Spectrometer with accumulating Electron Impact Ion Source" (PCT/US2011/048198) incorporated herein by reference in its entirety. For example, he co-pending application, contemplates a "closed" source that accumulates ions within the electron beam for a period of about 600 us, emits ion packets, passes them through the transfer optics and then accelerates ion packets by orthogonal accelerator into a multi-reflecting TOF MS. Note, that the described apparatus utilizes orthogonal acceleration as opposed to the direct pulsed extraction out of the source as discussed above. Experimentation suggests that the sensitivity was measured as 100 ions/fg in-spite of approximately 10-fold ion losses in the transfer ion optics. The electron beam storage capacity was saturating at approximately 100 pg/sec load at 600 us pulsing period. Thus, it may be estimated that the sensitivity of the direct extracting "closed" source as 1000 ions/fg and saturation limit of 2 ng/sec at 30 us period of single stage reflecting TOF. Accordingly, one may expect that the detection limit is rather limited by the chemical background, even accounting approximately 100-fold better immunity of "closed" source compared to prior art "open" pulsed sources.

It is recognized that concentration of analyte within closed sources may lead to earlier saturation of ion source storage capacity. Accordingly, the pulsed source may be operated at high extraction frequency, similarly to PCT/US2011/048198, incorporated herein by reference in its entirety. In one particular method, the pulse period is set shorter than the ion flight time in TOF MS, and a narrow mass range is selected by pulsed deflectors past the source. Such method is expected to surpass any possible effects of ion storage limitations by space charge and is expected to provide maximal sensitivity and dynamic range in trace analysis. In another particular method, similar to method of WO2011107836, incorporated herein by reference in its entirety, the frequent source pulsing is accompanied by encoding of pulsing time, such that the entire mass range spectrum can be recovered using a decoding algorithm. The above methods are particularly suitable in combination with multi-reflecting mass-spectrometers having an extended flight time, but much higher resolving power compared to regular time of flight instruments.

Further, in an embodiment, the analyte flow may be diluted to reduce the Helium flux into the ionization chamber and to improve the overall dynamic range of the EI analysis.

Referring now to FIG. 6, contrary to a sealed sample injection arrangement, an arrangement 62 is depicted whereby molecular separation occurs in-front of the "closed" pulsed source. As illustrated, the arrangement further includes a transfer line 63 for sealed sample injection, an inlet source skimmer 64, a transfer line 65 for spaced ion injection and an alignment piece 66.

In operation, in an embodiment, the transfer line 65 has an inner insert for axial alignment of a GC column inside (not shown and is aligned with the skimmer 64 using an aligning piece 66 (e.g., all at ground potential). In an embodiment, the distance between the transfer line 65 and the skimmer 64 is in the order of 1-3 mm, while skimmer aperture is in the order of 1 mm. Such scheme is expected to drop Helium flow into the skimmer and to enrich heavy analyte components, i.e. spatial losses of analyte molecules within an emerging helium jet are expected to be less than of Helium neutrals. However, even in the absence of the enrichment effects, the proposed scheme is expected to provide several benefits: (a) lower helium concentration within the source can reduce ion on gas scattering at ion pulsed extraction; (b) lower helium concentration may enhance ion storage capacity and reduce ion packet divergence; (c) somewhat lower flow of the sample may provide a match between maximal loads into micro-GC columns (approximately 10 ng into GC column) with extended storage limit of the source; and (d) improved EI spectra view (i.e., make such spectra closer to standard NIST library spectra.)

In an implementation, and as shown, excessive helium flow may be pumped away using a pumping chamber 67 and a pump 68, preferably a differentially pumping port of turbo pump 3P.

Referring to FIG. 7, in an implementation, the EI source vacuum chamber may be combined with the TOF MS analyzer chamber into a single vacuum chamber 3. For example, at 5-10-fold lower Helium flow (0.1-0.2 mL/min), the gas pressure in the combined vacuum chamber becomes less than 1E-5 Torr which is suitable for TOF MS with short flight path of 0.5-1m. In an implementation, the excessive Helium flow from GC or GCxGC 9 and via transfer line 8 may pumped down by differential port 76 of the dual port turbo pump 78, while the main port 77 is used for pumping vacuum chamber 3. A portion of helium flow and analyte flow are sampled via skimmer 74 at the entrance of the EI source 72. In addition, the entire instrument within single vacuum chamber ease several mechanical constrains.

Although the present invention has been describing with reference to preferred embodiments, it will be apparent to those skilled in the art that various modifications in form and detail may be made without departing from the scope of the present invention as set forth in the accompanying claims.

What I claim is:

1. A method of mass spectrometric analysis comprising:
separating an analyte mixture using two-dimensional gas chromatography to yield narrow (in-time) GC peaks;
introducing an analyte flow and a carrier gas flow into a closed electron impact ion source to form analyte ions, wherein the impact ion source includes an exit aperture;
sustaining enriched concentration of analyte molecules within said closed source by limiting an area of the exit aperture to between 0.1 and 1 cm$^2$;
accumulating said analyte ions within an electron beam of said closed electron impact ion source; and
pulse extracting ion packets from said closed source directly into a time-of-flight mass spectrometer.

2. A method as set forth in claim 1, wherein the source includes an inner liner having an isothermal cage disposed proximate thereto, the method further comprising:
maintaining the temperature of said source substantially uniform (within 10° C.).

3. A method as set forth in claim 1, wherein the closed source further comprises an inner surface having an area, and wherein a ratio of the area of the inner surface and the area of the exit aperture is between 10 and 100.

4. A method as set forth in claim 1, wherein the source includes a source vacuum chamber having a Peltier device disposed therein, the method comprising:
condensing vapors and fumes within the source vacuum chamber using a surface cooled by the Peltier device.

5. A method as set forth in claim 1, further comprising:
pumping down of a portion of carrier gas (inevitably causing some losses in the introduced sample amount) in front of said "closed" electron impact source.

6. A method as set forth in claim 1, wherein the closed source further comprising:
electrostatically repulsing analyte ions from sides of the source and along the direction of the electron beam.

7. A method as set forth in claim 1, wherein pulse extracting ion packets comprises:
operating at a high extraction frequency.

8. A method as set forth in claim 6, wherein time-of-flight mass spectrometer defines an ion time-of-flight, and wherein the pulse extraction defines a pulse period and further wherein the pulse period is shorter than the ion time-of flight.

9. A method as set forth in claim 8, wherein the mass spectrometer includes pulsed deflectors, the method comprising:
selecting a narrow mass range via the pulsed deflectors.

10. A chromato-mass spectrometer comprising:
a reflecting time-of-flight analyzer having an ion mirror, a free-flight region, and a detector;
a closed electron impact ion source defining one or more openings into an ionization chamber, wherein a cumulative area of the one or more openings into the ionization chamber is between 0.1 cm$^2$ and 1 cm$^2$, wherein the closed impact ion source includes a continuous electron beam, a repeller connected to a pulsed voltage supply and an extractor connected to the pulsed voltage supply, and wherein said ion mirror is aligned parallel with said detector and said closed ion source is tilted at small angle; and
a deflector for steering ion packets at an angle that is about equal to the source tilt angle.

11. An apparatus as set forth in claim 10, wherein the cumulative area of the one or more openings is selected from the group consisting of: (i) less than 100 mm$^2$, (ii) less than 50 mm$^2$, (iii) less than 20 mm$^2$; (iv) less than 10 mm$^2$; (v) less than 5 mm$^2$; (vi) less than 3 mm$^2$; and (vii) less than 1 mm$^2$.

12. An apparatus as set forth claim 10, wherein said closed electron impact ion source further comprises:
an inner chemically inert liner and an isothermal cage of heat conductive material.

13. An apparatus as set forth in claim 10, wherein said closed electron impact ion source has an inner surface defining an area, and wherein a ratio of the area of the inner surface and the area of the exit aperture is between 10 and 100.

14. An apparatus as set forth claim 10, further comprising:
a vacuum chamber; and
a cooling device arranged to chill a surface of the vacuum chamber to condense vapors and fumes therewithin.

15. An apparatus as set forth in claim 13, wherein the cooling device is a Peltier device.

16. An apparatus as set forth in claim 10, further comprising:
a skimmer provided at an entrance of the closed source;
a sample delivering transfer line spaced from said skimmer at a distance sufficient for reducing flow of carrier gas into said source by at least 5-fold.

17. An apparatus as in claim 16, wherein an excessive carrier gas is pumped down by a differential port of main turbo-pump, which pumps down said time-of-flight mass analyzer.

18. An apparatus as set forth in claim 10, further comprising:

means for repulsing ions along the sides of the ion chamber and along the direction of the electron beam.

19. An apparatus as set forth in claim 10, wherein the ion source includes an inner liner and the ion repulsing means includes a ceramic spacer isolating the ion chamber from the inner liner and defines an electrostatic bias and a push-low bias of repeller.

20. An apparatus as set forth in claim 10, wherein the ion source includes an inner liner and an emitter and the repulsing means is defined by positively biased slits disposed between the emitter and the inner liner.

21. An apparatus as set forth in claim 10, wherein the ion source includes an inner liner and an emitter having one or more positively biased slits to confine ions along the beam and to remove secondary ions.

* * * * *